United States Patent
Koh et al.

(10) Patent No.: US 7,465,953 B1
(45) Date of Patent: Dec. 16, 2008

(54) POSITIONING OF NANOPARTICLES AND FABRICATION OF SINGLE ELECTION DEVICES

(75) Inventors: Seong Jin Koh, Mansfield, TX (US); Choong-Un Kim, Arlington, TX (US); Liang-Chieh Ma, Arlington, TX (US); Ramkumar Subramanian, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 151 days.

(21) Appl. No.: 11/412,273

(22) Filed: Apr. 27, 2006

Related U.S. Application Data

(63) Continuation of application No. 11/327,885, filed on Jan. 9, 2006, now abandoned.

(60) Provisional application No. 60/642,294, filed on Jan. 7, 2005.

(51) Int. Cl.
*H01L 29/06* (2006.01)
*H01L 21/8234* (2006.01)

(52) U.S. Cl. ............................ 257/9; 257/213; 257/329; 257/E21.404; 438/142; 438/197; 438/268; 438/299

(58) Field of Classification Search ..................... 257/9, 257/213, 329, E21.404; 438/142, 197, 268, 438/299
See application file for complete search history.

(56) References Cited

U.S. PATENT DOCUMENTS 6,984,845 B2 * 1/2006 Khang .......................... 257/24

OTHER PUBLICATIONS

Subramanian, L-C. Ma, et al., "Fabrication of One-Dimensional Assemblies of Nanoparticles in a Wafer Scale," JSPS-UNT Joint Symposium on Nanoscale Materials for Optoelectronics and Biotechnology, University of North Texas, Feb. 2006.
Koh, S.J., "Controlled Positioning of Nanoparticles in a Wafer-Level," TMS Annual Meeting, San Antonio, TX, Mar. 2006.
Ma, L.-C, et al., "Wafer-Level Positioning of Nanoparticles using CMOS Technology and Wet Chemistry," Materials Research Society Spring Meeting, San Francisco, CA, Apr. 2006.

* cited by examiner

*Primary Examiner*—Evan Pert
(74) *Attorney, Agent, or Firm*—Gardere Wynne Sewell LLP

(57) ABSTRACT

The present invention includes single electron structures and devices comprising a substrate having an upper surface, one or more dielectric layers formed on the upper surface of the substrate and having at least one exposed portion, at least one monolayer of self-assembling molecules attracted to and in contact with the at least one exposed portion of only one of the one or more dielectric layers, one or more nanoparticles attracted to and in contact with the at least one monolayer, and at least one tunneling barrier in contact with the one or more nanoparticles. Typically, the single electron structure or device formed therefrom further comprise a drain, a gate and a source to provide single electron behavior, wherein there is a defined gap between source and drain and the one or more nanoparticles is positioned between the source and drain.

53 Claims, 11 Drawing Sheets

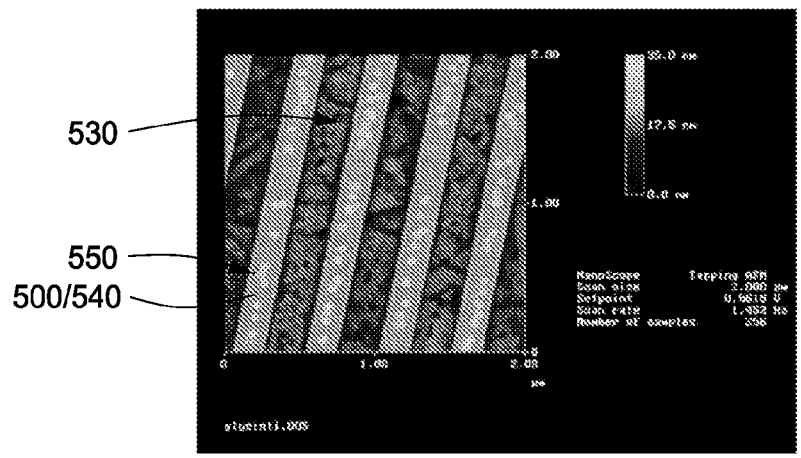
FIG. 6
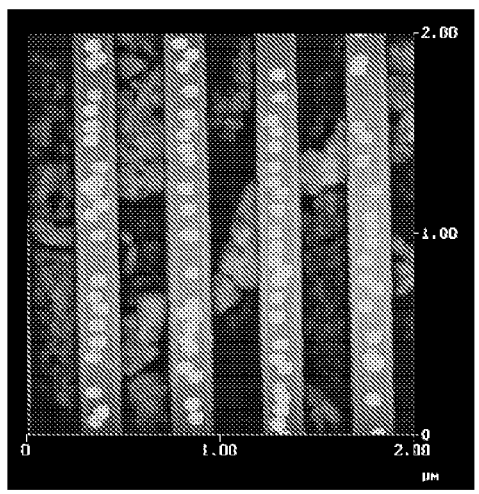
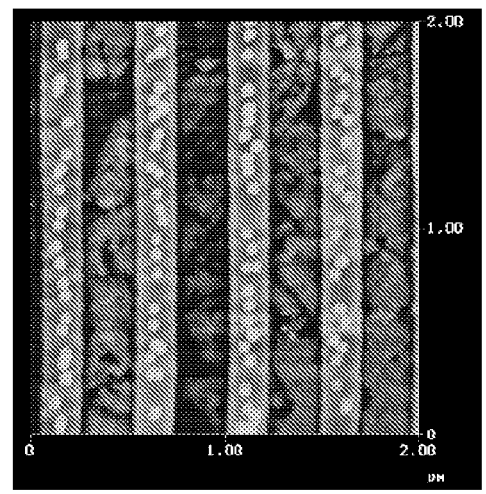
FIG. 7A  FIG. 7B

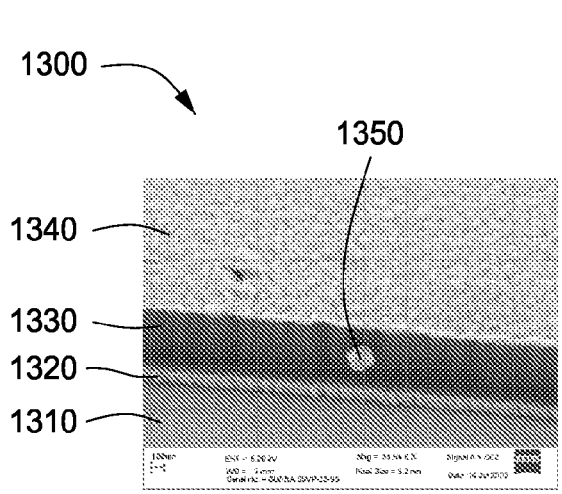
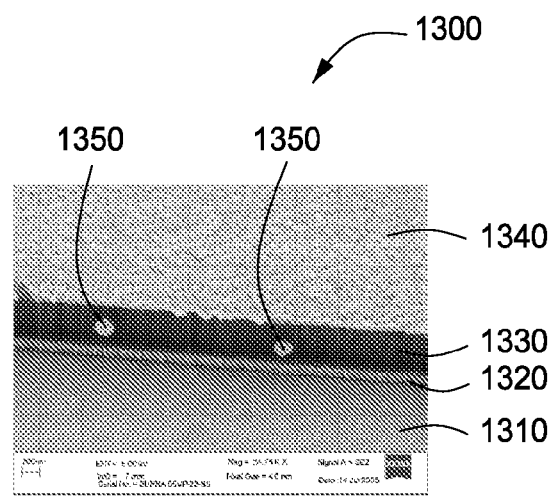
FIG. 13A  FIG. 13B
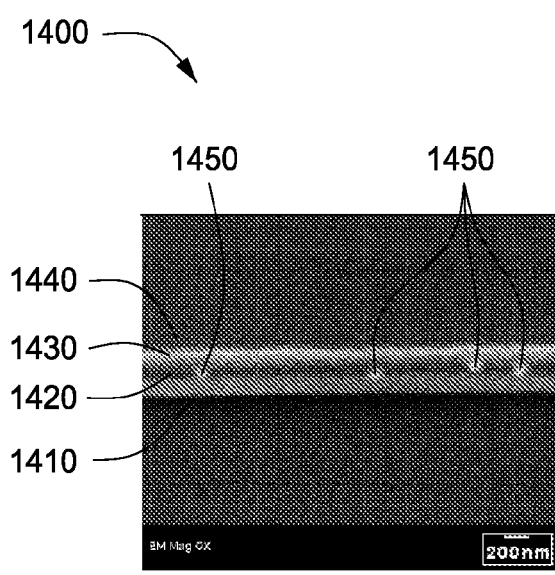
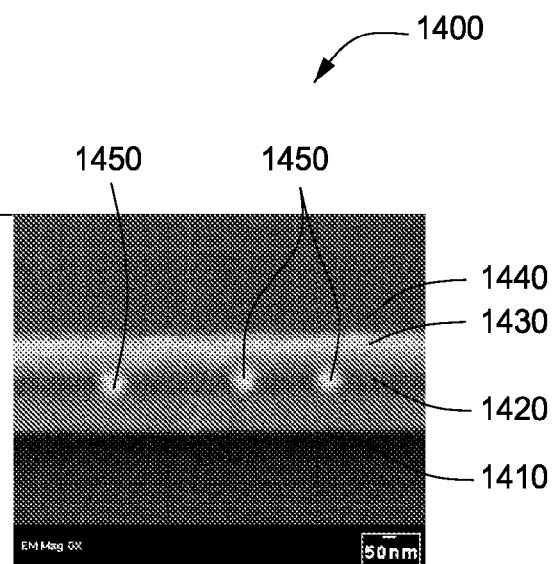
FIG. 14A  FIG. 14B

POSITIONING OF NANOPARTICLES AND FABRICATION OF SINGLE ELECTION DEVICES

CROSS-REFERENCES TO RELATED APPLICATIONS

This application is a continuation of prior U.S. application Ser. No. 11/327,885 filed Jan. 9, 2006, herein incorporated by reference.

BACKGROUND OF THE INVENTION

The present invention relates to the field of electronics, and more specifically to the fabrication of single electron devices on a nanometer scale.

With single electron technology, the transport of individual electrons should be precisely controlled. By operating with fewer electrons than current electronic devices, single electron technology makes it possible to fabricate extremely small electronic structures that offer several advantages, such as increasing sensitivity and conserving power, as examples.

Although the potential benefit of single electron technology is clear, the fabrication and the reliable production of addressable structures and devices therefrom is in its infancy. This is because a single electron device is inherently of nanoscale order and no current technique has been developed to fabricate such nanoscale elements at the wafer level.

The core element for this technology is a single electron transistor (SET). SET is a nanoscale structure generally comprising a source, a drain, a gate, and a charging island (Coulomb island) separated from the source and drain by tunneling barriers. To date, the requirement for geometric control with nanometer scale precision has stalled development of devices comprising SETs. Additional fabrication issues have hindered the implementation of SETs. For example, for room temperature operation, the size of the charging island and the thickness of the tunneling barriers of an SET must be in the nanometer range. Typical geometrical constraints are that (a) the distance between the source and drain electrodes needs to be controlled so that the separation is in the nanometer range, and (b) the charging island (Coulomb island) must be precisely positioned between source and drain electrodes to allow electron tunneling via the charging island.

To meet the above requirements, several techniques have been investigated, including e-beam lithography, the creation of gaps between two electrodes using electromigration, oxidation of metal film using scanning tunneling microscope (STM), and tailoring the gap of the two electrodes through electrochemical deposition. Unfortunately, none of these techniques have been able to consistently control the gap between the source and drain electrodes at the wafer level. For positioning charging islands between source and drain electrodes (constraint b), additional methods have been explored, including applying nanoparticles on predefined source and drain electrodes, creating nanoscale grains between source and drain electrodes without precise positioning control, using STM to define charging islands and tunneling barriers, or using AFM (atomic force microscopy) to create charging islands and tunneling barriers by applying mechanical force or voltage pulses. Unfortunately, these techniques are unable to precisely control the positioning of charging islands and when scanning probes are used, the techniques are too slow for practical application. The limitations have lead to the current inability to practically fabricate real and useful SETs at the wafer level.

As such, there remains a need for the fabrication of a usable single electron structure that is also practical, efficient, and economical and capable of being used for single electron devices. The fabrication technique should reliably control tunneling gaps between source and drain electrodes and provide for exact positioning of charging (Coulomb) islands as well as operate at room temperature.

SUMMARY OF THE INVENTION

The present invention solves current problems associated with fabricating single electron devices. Generally, the present invention provides for a single electron device structure and techniques for fabricating such a structure as well as devices comprising the structure.

Generally, and in one form, the present invention provides for a single electron structure capable of controlling nanoparticle (charging island) positioning and this nanoscale positioning of charging islands is provided relative to source, drain, and gate electrodes. With the single electron structure of the present invention, there is nanoscale control of the gap between source and drain electrodes by implementing a vertically aligned structure. By design, the single electron structure provides the controlled positioning of nanoparticles on selectively located self-assembled monolayers (SAMs). As such, the single electron structure and devices therefrom implement existing silicon fabrication technology and may be fabricated at the wafer level using such technologies as platforms. The present invention may also be mass produced using such technologies.

The present invention further provides for methods of fabricating a single electron structure and for a method of selective positioning of nanoparticles on a single electron structure comprising the steps of forming a self-assembled monolayer on a portion of a single electron structure, wherein the self-assembled monolayer is capable of selectively recognizing a portion of the single electron structure and contacting at least one nanoparticle for exhibiting single electron behavior.

The present invention also provides for a single electron structure comprising a substrate having an upper surface, one or more dielectric layers formed on the upper surface of the substrate and having at least one exposed portion, at least one monolayer of self-assembling molecules attracted to and in contact with the at least one exposed portion of only one of the one or more dielectric layers, one or more nanoparticles attracted to and in contact with the at least one monolayer, and at least one tunneling barrier in contact with at least one of the one or more nanoparticles. Typically, the single electron structure further comprises a drain, a gate and a source to provide single electron behavior, wherein there is a defined gap between source and drain and the one or more nanoparticles is positioned between the source and drain, the defined gap between source and drain being about 2 to 20 nm. The tunneling barrier is generally a dielectric layer or gaps between the nanoparticles and the drain and the nanoparticles and the source. The drain may be implanted on a portion of the substrate either before or after formation of the second dielectric layer. The nanoparticles comprise materials selected from the group consisting of semiconductor, metal, and combinations thereof. With the present invention, the single electron structure is capable of functioning as a device selected from the group consisting of electronic device, memory device, logic device, biologic sensor, chemical sensor, and combinations thereof and also capable of forming an integrated circuit.

The single electron structure of the present invention is capable of taking advantage of complementary metal-oxide semiconductor (CMOS) technology. Compositions and methods of the present invention are compatible with CMOS materials and processes. The present invention may be fabricated using a structure comprising CMOS. The present invention may be incorporated into existing CMOS circuits.

Features of the present invention provide for ultra-low power consumption devices, ultra-sensitive biological and chemical sensors, digital electronics (e.g., memories, logic devices), and detectors, as examples. Applications of the present invention include its commercial use (e.g., for electronics, telecommunications, biologic, pharmaceutical and chemical industries) and for military, space and security applications.

Those skilled in the art will further appreciate the above-noted features and advantages of the invention together with other important aspects thereof upon reading the detailed description that follows in conjunction with the drawings.

BRIEF DESCRIPTION OF THE DRAWINGS

For more complete understanding of the features and advantages of the present invention, reference is now made to the detailed description of the invention along with the accompanying figures, wherein:

FIG. 6 illustrates controlled positioning of nanoparticles in accordance with one aspect of the present invention as viewed by atomic force microscopy (AFM);

FIGS. 7A and 7B illustrate controlled positioning of nanoparticles in accordance with another aspect of the present invention, including (A) an AFM view after controlled positioning of nanoparticles on a self-assembled monolayer structure and (B) an AFM view after removal of the self-assembled monolayer structure;

FIGS. 13A and 13B illustrate controlled positioning of nanoparticles in a patterned single electron structure and device of the present invention as viewed by scanning electron microscopy (SEM); and FIGS. 14A and 14B illustrate another aspect of the present invention depicting controlled positioning of nanoparticles in a patterned single electron structure and device of the present invention as viewed by SEM.

DETAILED DESCRIPTION OF THE INVENTION

Figure 1A:
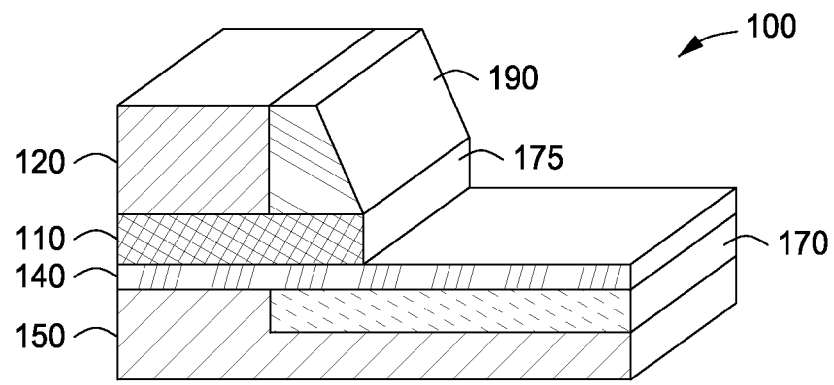
FIGS. 1A-1C depict schematics for fabrication of a single electron structure and device in accordance with one aspect of the present invention, including (A) a starting structure, (B) providing a self-assembled monolayer on a nanoscale dielectric layer (layer 110) with a nanoparticle, and (C) another dielectric layer that has been deposited and a source.

Although making and using various embodiments of the present invention are discussed in detail below, it should be appreciated that the present invention provides many inventive concepts that may be embodied in a wide variety of contexts. The specific aspects and embodiments discussed herein are merely illustrative of ways to make and use the invention, and do not limit the scope of the invention.

In the description which follows like parts may be marked throughout the specification and drawing with the same reference numerals, respectively. The drawing figures are not necessarily to scale and certain features may be shown exaggerated in scale or in somewhat generalized or schematic form in the interest of clarity and conciseness.

In general, the present invention takes advantage of some features of a single electron transistor (SET), the present invention comprising a single electron structure with a substrate having a surface and functioning with a source, a drain, a gate, and a charging island (also referred to as a Coulomb island). The charging island of the present invention is separated from source and drain by at least one tunneling barrier. In a SET, an electron tunnels through the tunneling barrier from the source to the charging island, and then from the charging island to the drain. This transport is typically controlled by the nearby gate. If the size of a charging island is small enough, the energy required to add a single electron to the charging island becomes greater than the thermal energy, resulting in the blockade of electron tunneling (Coulomb blockade effect). With the present invention, by adjusting the bias voltage V (between the source and drain) and gate voltage $V_G$, which changes the electrostatic potential of the Coulomb island relative to source and drain, the blockade of electron tunneling is controlled and the number of extra electrons in the Coulomb island is precisely regulated as is the average frequency of electrons tunneling through the Coulomb island.

An SET is necessarily a nanoscale structure. For the single electron device of the present invention to operate at room temperature, the size of the Coulomb island is in the nanometer range and the thickness of the tunneling barriers is at least about a few nanometers or less.

Single Electron Structure

Figure 1B:
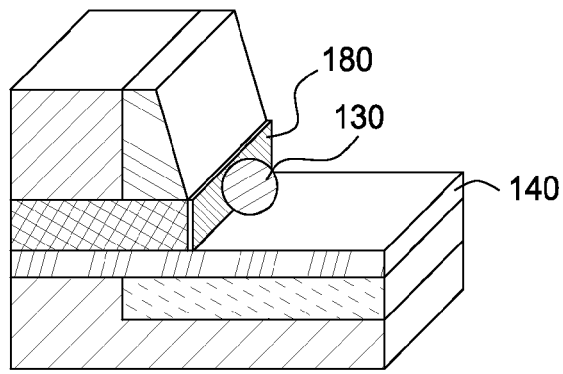
Figure 1C:
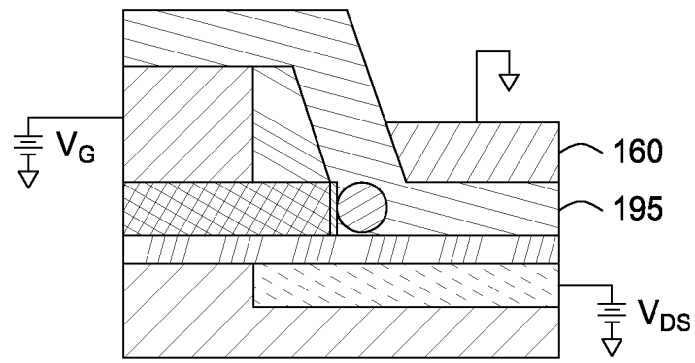

Schematics of a single electron structure and device and fabrication of such structures and devices of the present invention are illustrated in FIGS. 1A-1C. Typically, a structure 100 comprises substrate 150 having an upper surface (FIG. 1A). As is known to those having skill in the art, the substrate may comprise monocrystalline silicon, semiconductor-on-insulator (SOI), silicon carbide, gallium arsenide, gallium nitride, diamond thin film, glass, polymeric material (e.g., plastic) and/or other suitable materials, and may also include one or more heteroepitaxial and/or homoepitaxial layers on the substrate. The upper surface of the substrate may be planar or non-planar (three-dimensional).

In contact with the upper surface of substrate 150 is at least one nanoscale dielectric layer, such as second dielectric layer 110, and at least one tunneling barrier, such as first dielectric layer 140 (FIG. 1A). First dielectric layer 140 is typically a different material than second dielectric layer 110. A third dielectric layer 190 is deposited, defined and in contact with at least a portion of second dielectric layer 110; the material of third dielectric layer 190 is typically a different dielectric material than second dielectric layer 110. To function, structure 100 is constructed with nanometer scale precision with a surface of substrate 150 in contact with first dielectric layer 140 of which a portion is in contact with second dielectric layer 110 and third dielectric layer 190. Source 160, drain 170, gate 120 and at least one charging island 130 (a Coulomb island) are provided as shown in FIG. 1B and 1C. The at least one charging island 130 may be in direct contact with a portion of second dielectric layer 110 (e.g., exposed sidewall 175) or in contact with a self-assembled monolayer 180 that has formed on a portion of second dielectric layer 110. While only one unit of structure 100 is shown in FIG. 1A-1C, an integrated circuit may be fabricated in parallel. In particular, structure 100 may be fabricated in a CMOS framework.

In general, fabrication of structure 100 includes the following parameters: (a) the distance between source 160 and drain 170 electrodes are controlled and at least about 10 nm and may be less than 10 nm; (b) the distance between source 160 and drain 170 electrodes depends on the size of one or more charging islands 130 and the thickness of one or more tunneling barriers (e.g., first dielectric layer 140, fourth dielectric layer 195); (c) charging island 130 must be precisely positioned between source 160 and drain 170 electrodes to allow electron tunneling via the charging island 130.

In one embodiment, a single electron device and structure is fabricated as shown in FIGS. 1A-1C. In this embodiment, the thickness of first dielectric layer 140 and second dielectric layer 110 are in the nanometer range, preferably at least about 2 nm and at least about 5 nm, respectively. Nanoscale dimensions of these two layers are possible using deposition and/or oxidation technology as known to one of ordinary skill in the art. These technologies allow the thickness of the dielectric layers to be controlled to within a few angstroms. By controlling the thickness of these layers at nanoscale or sub-nanoscale dimensions, the present invention achieves precise control in defining the distance between the source and drain. The present invention does not have to rely on controlling the lateral dimension at a nanoscale level. First dielectric layer 140 is typically a dielectric that acts as a tunneling barrier between drain 170 and charging island 130. The exposed sidewall 175 of second dielectric layer 110 serves as a surface on which an additional component, a self-assembled monolayer (SAM) structure 180, when provided may come in contact with, bind to and/or attach.

Self-Assembled Monolayer (SAM) Structure

SAM structure 180 comprises an organic or inorganic molecule or compound with a tail group that holds electric charge, such as an amino group ($-NH_2$ with a positive charge) or carboxyl group ($-COOH$ with a negative charge). The molecule selected is one that has an affinity for nanoparticle adhesion and must be capable of forming a monolayer-like structure. When the molecules form as SAM structure 180, structure 180 when provided to the present invention is capable of contacting second dielectric layer 110. Typically, contact of a SAM structure 180 with second dielectric layer 110 includes surface attachment or chemical bonding of surface atoms of second dielectric layer 110 with molecules forming SAM structure 180. Molecules forming SAM structure 180 do not typically contact, attach, or bind to first dielectric layer 140 or other dielectric surfaces of structure 100 (e.g., spacer 190). Therefore the charged group of SAM structure 180 terminates only on second dielectric layer 110 as shown in FIG. 1B.

Nanoparticle Charging Island

The single electron transistor structure 100 of FIG. 1A is capable of contacting at least one nanoparticle (as a charging island 130) as depicted in FIG. 1B. The thickness of second dielectric layer 110 and the contact between this layer and SAM structure 180 help control the alignment of nanoparticles (i.e., charging island 130) and enable nanoscale positioning of charging islands 130 relative to source 160, drain 170, and gate 120 electrodes.

Nanoparticles of the present invention are of an opposite charge to SAM structure 180 and are able to contact SAM structure 180. This contact is typically through an electrostatic interaction. Nanoparticles may be semiconductor nanoparticles or metal nanoparticles. Metal nanoparticles are typically selected from the group consisting of noble metals, alkali metals, alkaline earth metals, Group III metals, transition metals, and Group IV metals. The nanoparticles are prepared by techniques known to one of ordinary skill in the art. In one embodiment, a colloidal solution of oppositely charged nanoparticles is allowed to contact structure 100 after immersion of structure 100 into the colloidal solution. The contact and number of contacting nanoparticles is controlled by varying the concentration of the colloidal solution and/or varying the immersion time.

Fabrication of Single Electron Device

Single electron structures of the present invention are fabricated to form working structures (i.e., single electron devices). Single electron structures of the present invention may also be single electron devices. For fabrication of a single electron structure, such as structure 100 as depicted in FIG. 1A, it initially comprises first dielectric layer 140 and second dielectric layer 110 with drain 170 and gate 120 on substrate 150. First dielectric layer 140 is typically at least about 2 nm and acts as a tunneling barrier. Second dielectric layer 110 is at least about 5 nm. An additional component of structure 100 as shown in FIG. 1B typically includes third dielectric layer 190. In FIGS. 1A-1C, substrate 150 is typically a monocrystalline silicon, but may comprise a material as previously described.

To form SAM structure 180 on second dielectric layer 110 as shown in FIG. 1B, SAM structure 180 is composed of one or more organic molecules containing functionalized groups (e.g., amino group) at one end capable of holding an electric charge. The other molecular end of SAM structure 180 attaches to the surface atoms of second dielectric layer 110, but does not attach to third dielectric layer 190 or first dielectric layer 140. A colloidal solution comprising charged nanoparticles is prepared by known methods (e.g., Foss, C A and Feldheim D L, 2001, "Metal Nanoparticles: Synthesis, Characterization, and Application," Dekker, NY, N.Y.) and structure 100 is dipped into the colloidal solution. Charged nanoparticles then selectively adhere to the exposed sidewall of second dielectric layer 110 that had been functionalized with the charged SAM structure 180 as shown in FIG. 1B. A fourth dielectric layer 195 comprising a dielectric material such as high-density plasma (HDP) oxide is then deposited on structure 100, as shown in FIG. 1C, followed by formation of a source 160 electrode (FIG. 1C). Fourth dielectric layer 195 acts as a tunneling barrier between source 160 and charging island 130.

As evidenced by FIGS. 1A-1C, the following are features of the present invention: (a) the distance between the source and drain electrodes is controlled with nanometer and/or sub-nanometer precision; (b) the charging island is precisely positioned such that the distance between the charging island and the three electrodes (source, drain, and gate) is controlled on a nanometer or sub-nanometer scale; and (c) once the single electron structure of the present invention is fabricated, interconnections among individual single electron structures may be processed to produce an integrated circuit. Processing is designed to take advantage of current technologies, including CMOS fabrication technology.

Figure 2A:
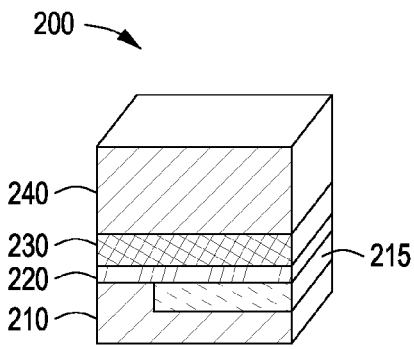
FIGS. 2A-2I depict schematics for fabrication of a single electron structure and device in accordance with another aspect of the present invention, including (A) a starting structure comprising nanoscale dielectric layers, (B) forming a gate, (C) depositing another dielectric layer, (D) forming a spacer, (E) etching one of the initial dielectric layers, (F) providing a self-assembled monolayer structure on the etched dielectric layer, (G) providing nanoparticles for contact with the self-assembled monolayer structure, (H) a side view of (G), and (I) depositing another dielectric layer and providing a source.

FIGS. 2A-2I represents another embodiment of the present invention that details fabrication of a single electron structure and device. As shown in FIG. 2A, structure 200 comprises a semiconductor substrate or wafer 210 on top of which a drain 215 is defined through ion implantation as well as dopant activation through rapid thermal annealing which is typically followed by wet cleaning of the surface. In an alternative, ion implantation may be performed after etching second dielectric layer 230 (see FIG. 2E). In this case, a portion of first dielectric layer 220 (in contact with drain 215) is removed typically by chemical etching and then cleaned. A new first dielectric layer 220 may need to be re-grown (e.g., via thermal oxidation) on top of drain 215. This process of removal, cleaning and re-growth is known to one of ordinary skill in the art.

On top of the wafer 210 and drain 215 a first dielectric layer 220 is grown or deposited using techniques known in art. Growth techniques may include thermal oxidation or rapid thermal processing and deposition techniques may include plasma enhanced chemical vapor deposition [PECVD] or atomic layer deposition [ALD]). On top of first dielectric layer 220, second dielectric layer 230 is deposited, followed by deposition of gate 240 typically comprising a polysilicon film.

Figure 2B:
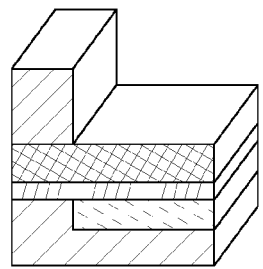
Figure 2C:
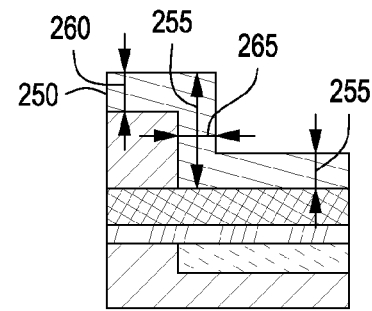

Gate 240 is defined using photolithography and reactive ion etching (RIE), as shown in FIG. 2B. After etching, a third dielectric layer 250 is deposited (FIG. 2C). Again, deposition may be performed using techniques known in the art, such as PECVD and ALD. Third dielectric layer 250 may have a vertical dimension that is larger along the sidewall of gate 240, as indicated by arrow 255, because typical deposition processes produce conformal films, wherein the thickness of the film is substantially uniform along corrugated and non-corrugated surfaces, as indicated by shorter arrows 260, 265, and 270. This dimensional relationship is not imperative for proper functioning of the single electron structure or device.

Figure 2D:
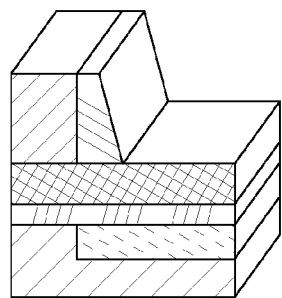

Third dielectric layer 250 is then etched using RIE, anisotropically etching the material in the vertical direction (FIG. 2D). This anisotropic etch leaves a portion of the third dielectric layer 250 or spacer 275 along the sidewall of gate 240. The present invention may take advantage of an etching technique known in the art (also referred to as spacer etch) that is frequently used in metal-oxide-semiconductor field-effect-transistor (MOSFET) fabrication. By using the previously described steps, the method of the present invention is able to control the width of spacer 275 with nanometer scale resolution, e.g., by varying the initial deposition thickness of third dielectric layer 250, by adjusting parameters during RIE, and/or by adjusting the initial thickness of gate 240. Currently there is no alternative method that is practical and reliable and defines lateral dimensions with nanometer resolution.

Figure 2E:
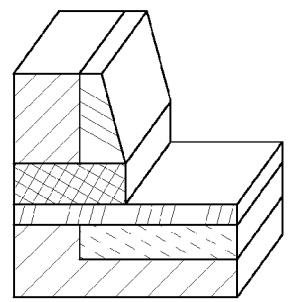

As illustrated in FIG. 2E, a portion of second dielectric layer 230 is then etched providing an exposed surface of first dielectric layer 220. Typically, the etching is performed without a mask, because gate 240 and spacer 275 act as the mask. As an alternative, after etching second dielectric layer 230, an exposed portion of first dielectric layer 220 in contact with drain 215 may be removed, followed by cleaning the remaining surface and then re-growing first dielectric layer 220 on top of drain 215. In some instances, this alternative method may provide a higher quality tunneling barrier.

Figure 2F:
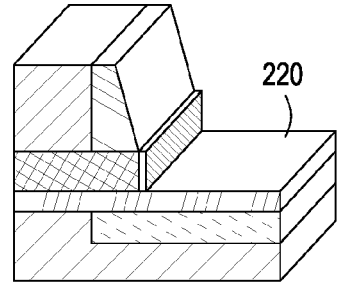
Figure 2G:
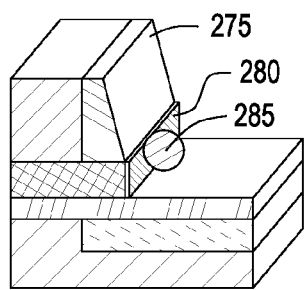
Figure 2H:
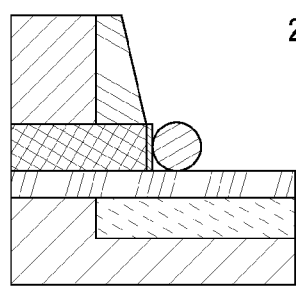
Figure 2I:
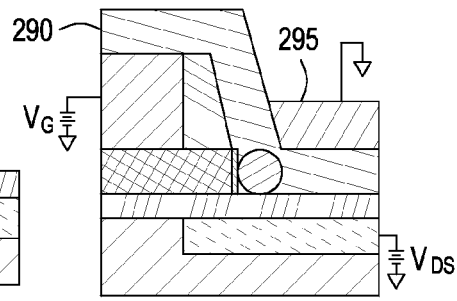

A self-assembled monolayer 280 was then provided and formed on the sidewall surface of second dielectric layer 230 as shown in FIG. 2F. Self-assembled monolayer 280 is selected based on the choice of the dielectric layers deposited on structure 200 and selection requires no undue experimentation. Self-assembled monolayer 280 must hold an electric charge, be selective for second dielectric layer 230, and selectively form on second dielectric layer 230. After assembly of monolayer 280, substrate 200 is immersed in a colloidal solution of charged nanoparticles 285. Because charged nanoparticles 285 are of an opposite charge to monolayer 280, nanoparticles 285 selectively contacted monolayer 280, typically through an electrostatic interaction (FIGS. 2G and 2H). This is followed by deposition of fourth dielectric layer 290 (such as an oxide layer) and formation of a source electrode 295 as depicted in FIG. 2I. The thickness of fourth dielectric layer 290 is typically a few nanometers and controlled with sub-nanometer precision. As such fourth dielectric layer 290 functions as a tunneling barrier between source electrode 295 and the Coulomb island comprising nanoparticles 285.

For the fabrication of an integrated circuit comprising structure 200 (or any other single electron device described herein), process steps include those described in FIGS. 2A-2I after which typical CMOS fabrication steps may be relied upon. Formation of the dielectric layers, formation of one or more self-assembled monolayers, and the contacting of nanoparticles to the self-assembled monolayer(s) of the present invention are compatible with current CMOS fabrication processes. In fact, fabrication of the present invention can be readily and easily integrated into current CMOS manufacturing flow.

With the present invention, there is a well-defined gap between source electrode 295 and drain electrode 215. This is typically at least about 10 nm. In addition, nanoparticles 285 (e.g., Coulomb island) that lie between source 295 and drain 215 are precisely positioned. Further, there is a well-controlled distance between gate 240 and nanoparticles 285 (Coulomb island).

Monolayer Self-Assembly and Alignment of Nanoparticles

Additional features of the present invention include (a) selective formation of at least one self-assembled monolayer on one dielectric layer, the layer being equivalent to second dielectric layer 110 of FIG. 1 or second dielectric layer 230 of FIG. 2 and (b) alignment of nanoparticles on the formed self-assembled monolayer of (a).

As presented, molecules that comprise the monolayer of (a) above are also selected with the following criteria: (1) capable of self-assembly; (2) have a head group to contact a dielectric layer and a tail group with a charge; (3) recognize and contact only one of the dielectric layers, the layer being equivalent to second dielectric layer 110 of FIG. 1 or second dielectric layer 230 of FIG. 2; and (4) do not contact layers comprising the spacer (equivalent to third dielectric layer 190 of FIG. 1 or spacer 275 of FIG. 2) or tunneling barriers (equivalent to first dielectric layer 140 of FIG. 1 or first dielectric layer 220 of FIG. 2).

Figure 3A:
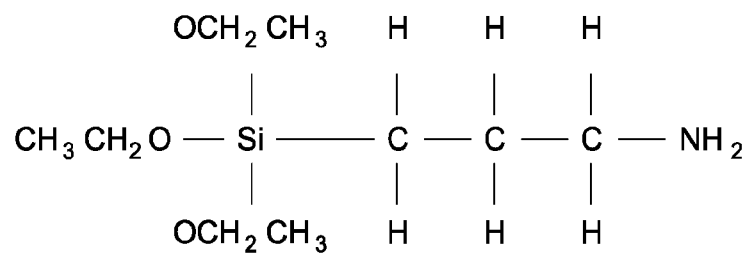
FIGS. 3A-3C depict (A) a molecular structure capable of forming a self-assembled monolayer in accordance with one aspect of the present invention, (B) gold nanoparticles on the self-assembled monolayer in contact with a dielectric layer comprising a silicon dioxide wafer, and (C) the absence of a self-assembled monolayer and gold nanoparticles on a dielectric layer comprising silicon nitride.

An example of the selective formation of a self-assembled monolayer and alignment of nanoparticles begins with two initial materials (wafers) forming a single electron structure. The dielectric materials used in one embodiment included silicon oxide and silicon nitride. Self-assembled monolayer were provided using 3-aminopropyltriethoxysilane (APTES). The chemical structure of APTES is illustrated in FIG. 3A showing a charged tail with an amino group ($-NH_2$) and a silane head group. APTES molecules recognize silicon dioxide surfaces and form self-assembled monolayers terminating with an amine group when in contact with a silicon dioxide surface. Contact of the APTES molecule with silicon dioxide includes formation of a chemical bond between the oxygen atom in silicon dioxide and the silicon atom in the silane head group of APTES. For example, when two wafers, one with silicon dioxide and the other with silicon nitride were immersed in a solution containing APTES, self-assembled monolayers formed on the silicon dioxide wafer and not the silicon nitride wafer.

Figure 3B:
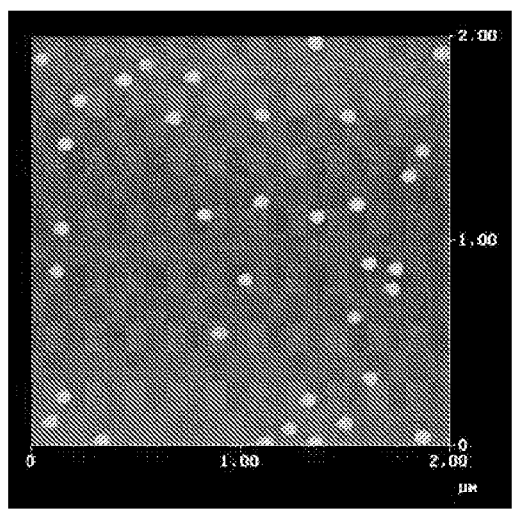
Figure 3C:
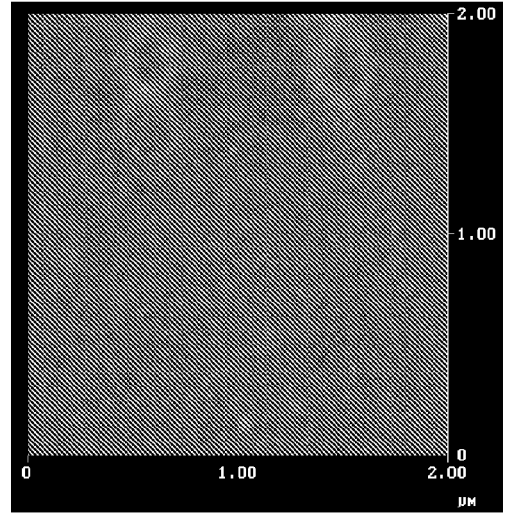

After self-assembly of an APTES monolayer onto the silicon dioxide surface, the wafer was immersed into a colloidal solution of gold nanoparticles that were negatively charged. Gold nanoparticles were attracted to the APTES monolayer (positively charged with amine groups) but were not attracted to the silicon nitride surface. FIG. 3B illustrates the attraction and contact of gold nanoparticles to the APTES monolayer that formed on silicon dioxide as viewed using atomic force microscopy. FIG. 3C illustrates the absence of gold nanoparticles on a silicon nitride surface viewed by AFM. The lack of gold nanoparticles on the silicon nitride surface was because silane groups in APTES do not recognize or contact a silicon nitride surface, thus there was no monolayer formation. As such, silicon dioxide may be used as second dielectric layer 230 as shown in FIG. 2 and silicon nitride may be used as first dielectric layer 220 or third dielectric layer 250 as shown in FIG. 2.

Figure 4A:
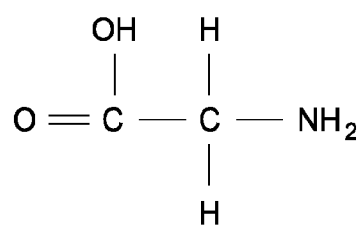
FIGS. 4A-4D depict (A) a molecular structure capable of forming a self-assembled monolayer in accordance with another aspect of the present invention, (B) gold nanoparticles on the self-assembled monolayer in contact with a dielectric layer comprising aluminum oxide, (C) the absence of a self-assembled monolayer and gold nanoparticles on a dielectric layer comprising silicon oxide, and (D) the absence of a self-assembled monolayer and gold nanoparticles on a dielectric layer comprising silicon nitride.

In yet another example of monolayer self-assembly and alignment of nanoparticles, three dielectric materials were used—silicon dioxide, silicon nitride, and aluminum oxide. Glycine was used as the molecule forming a monolayer, as illustrated in FIG. 4A. Glycine has an amino group at its tail and a carboxyl group as the head group. The carboxyl group head of glycine recognized and contacted the surface of aluminum oxide wafer, allowing glycine to form a self-assembled monolayer on aluminum oxide surfaces. A self-assembled monolayer did not form on wafers comprising silicon dioxide or silicon nitride.

Figure 4B:
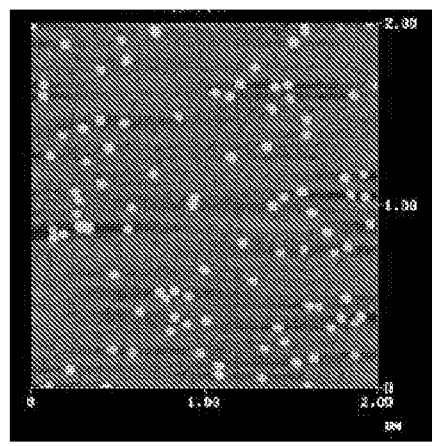
Figure 4C:
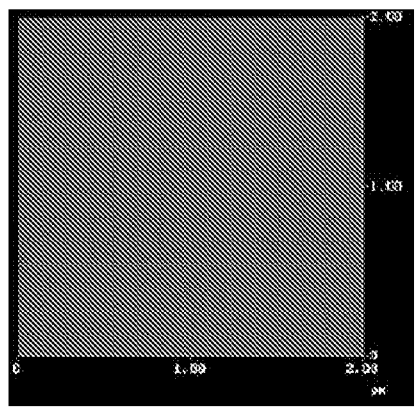
Figure 4D:
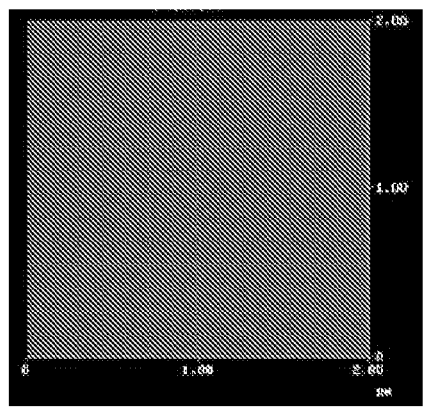
Figure 5A:
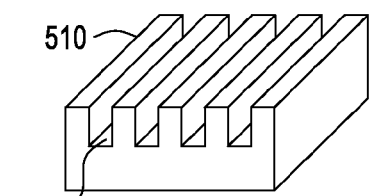
FIGS. 5A-5E depict schematics for controlled positioning of nanoparticles in accordance with one aspect of the present invention, including (A) trench formation, (B) electrochemical deposition of a metal, (C) Chemical Mechanical Polishing (CMP), (d) providing a self-assembled monolayer structure on the dielectric layer, and (e) providing nanoparticles on the self-assembled monolayer structure.
Figure 5B:
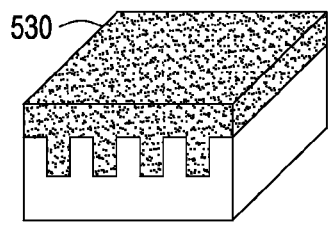
Figure 5C:
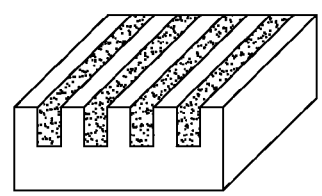
Figure 5D:
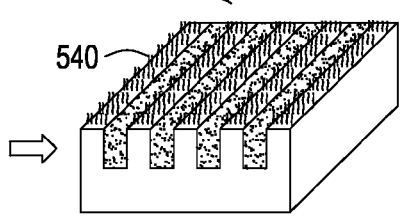
Figure 5E:
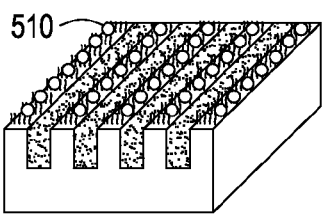

Wafers of silicon dioxide, silicon nitride or aluminum oxide were immersed in a colloidal solution containing gold nanoparticles. FIG. 4B shows that gold nanoparticles contacted the glycine monolayer formed on aluminum oxide, as viewed by AFM. Gold nanoparticles did not attach to the silicon dioxide wafer (FIG. 4C) or silicon nitride wafer (FIG. 4D) because glycine did not form a self-assembled monolayer on these dielectric materials. Aluminum oxide may then be used as second dielectric layer 230 as shown in FIG. 2, while silicon dioxide or silicon nitride may be used as first dielectric layer 220 and/or third dielectric layer 250 as shown in FIG. 2. An advantages of aluminum oxide it that it provides a high quality dielectric layer that can be selectively etched when other materials are used as first dielectric layer 220 (e.g., silicon oxide, silicon nitride). For example, during RIE (as shown in FIG. 2E), selective etching will remove portions of second dielectric layer 230 without affecting first dielectric layer 220.

Further illustrations that nanoparticles are capable of self aligning on self-assembled monolayers formed on nanoscale sidewalls of the dielectric layer of the present invention are represented in FIGS. 5, 6 and 7. In FIG. 5A, a wafer comprising a dielectric layer 500 (equivalent to second dielectric layer 110 of FIG. 1 or second dielectric layer 230 of FIG. 2) was plasma etched to provide alternating raised (exposed) surfaces 510 and recessed surfaces 520, wherein raised surfaces 510 form narrow strips. A second material 530 was deposited on top of dielectric layer 500, some of the second material 530 forming into recessed surfaces 520 (FIG. 5B). The structure was then polished using CMP until dielectric layer 500 was exposed A monolayer 540 that is selective for raised surface 510 was allowed to form on the surface of the structure of 5C (FIG. 5D) after which wafer 560—the structure of 5D—was immersed in a colloidal solution comprising nanoparticles 550. Nanoparticles 550 were found to contact only surfaces previously contacted by monolayer 540, that being raised surface 510 (FIG. 5E).

Wafer 560 was fabricated with dielectric layer 500 as a porous carbon-containing silicon oxide and second material 530 as copper. A self-assembled monolayer comprising APTES molecules was provided and formed as monolayer 540 only on raised surfaces 510 (and not on copper surfaces) as shown in FIG. 6. After immersion in an aqueous solution of nanoparticles 550 as 20 nm gold nanoparticles (white dots in FIG. 6), nanoparticles 550 selectively contacted and were aligned on the APTES monolayer that had formed on silicon oxide portion. No gold nanoparticles were found on the copper portion of the wafer. Instead, gold nanoparticles typically positioned in the center area of the silicon oxide portion, in part, from an electric field gradient moving towards the center of the porous carbon-containing silicon oxide.

As discussed, the quantity and alignment of nanoparticles may be controlled by a number of ways, including varying the immersion time and the concentration of nanoparticles. Many nanoparticles are also typically separated from each other due to repulsive electrostatic forces between them. For example, gold nanoparticles that are at least about 20 nm in diameter will generally have a separation of at least about 40 nm from another like nanoparticle.

Integrity of Nanoparticles

With the present invention, specifically aligned nanoparticles are highly stable after contacting a self-assembled monolayer. In fact, with the present invention, the self-assembled monolayer may be subsequently removed after the one or more nanoparticles have contacted the single electron structure. Removal of the self-assembled monolayer is typically performed before addition of the second tunneling barrier (equivalent to fourth dielectric layer 195 of FIG. 1 or fourth dielectric layer 290 of FIG. 2). The integrity of nanoparticles on surfaces of single electron structures of the present invention is illustrated in FIG. 7. Here, self-assembled monolayers were removed from the surfaces of single electron structures after nanoparticles were provided and assembled on the monolayers. Typically, self-assembled monolayers may be removed by any of several techniques known in the art, such as applying oxygen plasma using an asher, a technique similar to that used to remove photoresist in CMOS fabrication, and/or by ultrasonic agitation. In FIG. 7A, one of several AFM images was taken of wafer 560 on which gold nanoparticles (white circles) had selectively attached on the self-assembled monolayer formed on porous carbon-containing silicon oxide. After removal of monolayer 540 using an asher which was followed by ultrasonic agitation in methanol, a second set of AFM images were taken as shown in FIG. 7B. As such, FIG. 7B illustrates that removal of the monolayer from wafer 560 (a) did not remove nanoparticles 550 (white circles) and (b) did not change the density of nanoparticles 550 on the surface of wafer 560. In addition, nanoparticles 550 did not relocate to another portion of wafer 560, but remained at raised surfaces 510 comprising porous carbon-containing silicon oxide. Nanoparticles 550 remain attracted to raised surfaces 510 via attracted forces, such as Van der Waals interactions.

Fabrication of Single Electron Memories

Figure 8A:
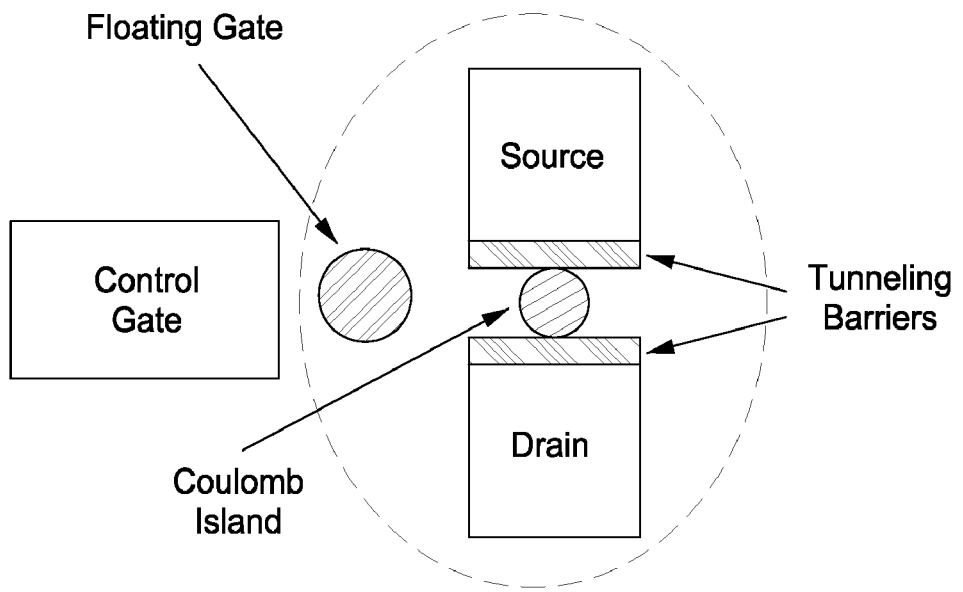
FIGS. 8A and 8B depict schematics of (A) a floating gate single electron memory in accordance with one aspect of the present invention and (B) the corresponding circuit diagram.
Figure 8B:
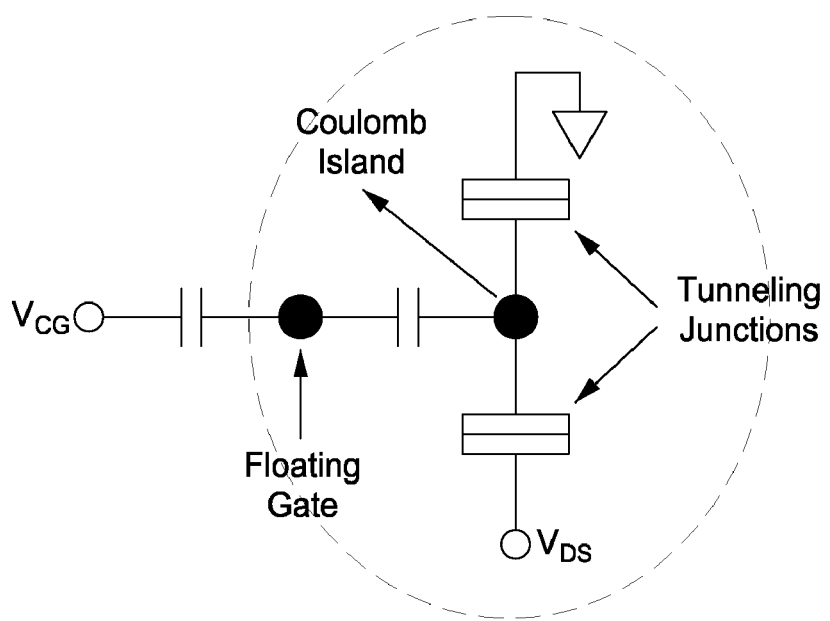

Single electron structures of the present invention may be fabricated into single electron memory devices as illustrated in FIG. 8, in which the device is a floating gate single electron memory device. In single electron memory, one bit is represented by only a few or a few tens of electrons in the floating gate and its charge is detected using an SET. Because only a small number of electrons are involved in charging as well as sensing, the single electron memory can operate with extremely-low power consumption.

Fabrication of such single electron memories is an extension of the fabrication described in FIG. 2 and illustrated in FIG. 9. Here, fabrication begins with a single electron structure 900 with a substrate 950 having an upper surface further comprising a first dielectric layer 920 in contact with the upper surface, a second dielectric layer 910 defined and in contact with a portion of tunneling barrier 920 with a drain 930 and a third dielectric layer 940 defined and in contact with second dielectric layer 910 (FIG. 9A). The vertical dimension of third dielectric layer 940 may be larger than the lateral dimension that is in contact with second dielectric layer 910. This dimensional characteristic is not a requirement of single electron structures of the present invention. Substrate 950 is typically monocrystalline silicon, but may comprise any material as previously described.

Figure 9A:
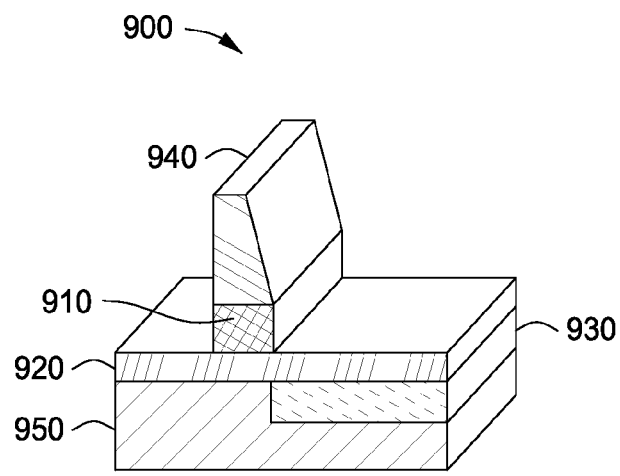
FIGS. 9A-9D depict schematics for a floating gate single electron memory in accordance with one aspect of the present invention, including (A) a starting structure, (B) a dielectric layer in contact with a self-assemble monolayer structure in contact with nanoparticles, (C) another view of (B), and (D) another dielectric layer, a control gate and a source.
Figure 9B:
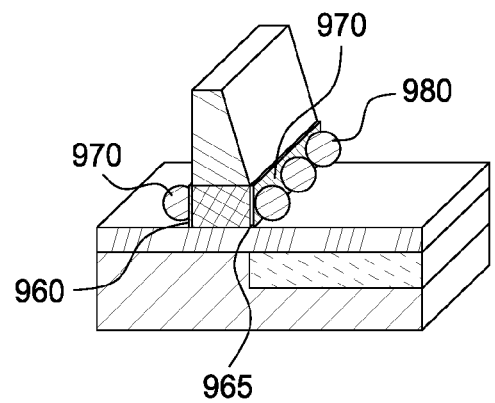
Figure 9C:
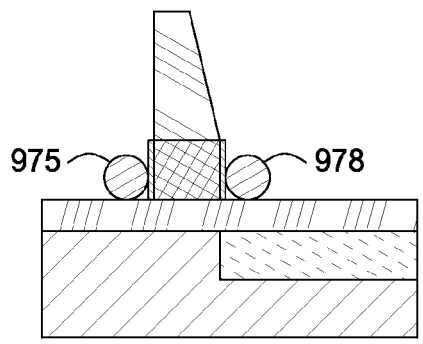
Figure 9D:
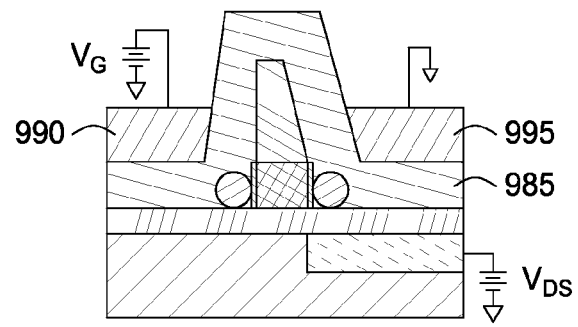

Second dielectric layer 910 contains two exposed sidewalls 960 and 965. The thickness of second dielectric layer 910 is typically less than 10 nm and may be at least about 5 nm or less. In one aspect of the present invention, the thickness depends on the size of the nanoparticle. The thickness of first dielectric layer 920 is also less than 5 nm and may be at least about 2 nm or less. In FIG. 9B, a self-assembled monolayer 970 (equivalent to that described for FIG. 2) is allowed to form on the exposed sidewalls 960 and 965 of second dielectric layer 910. This is followed by immersion of structure 900 in a solution of nanoparticles to promote contact and alignment of nanoparticles 980 with self-assembled monolayer 970. Nanoparticles 980 act as a Coulomb island 978 (charging island) as well as floating gate 975, as shown in FIG. 9C which is a side view of FIG. 9B. The memory structure then receives a fourth dielectric layer 985, typically through deposition. Fourth dielectric layer 985 is formed on the surface of third dielectric layer 940, charging island 978 and floating gate 975 and acts as a tunneling barrier. This is followed by formation of control gate 990 and source 995. The memory structure may then be fabricated further, as needed, using techniques known in the art. For example, the memory structure may be fabricated into an integrated circuit of single electron memories or other such multi-purpose circuit.

Chemical and Biologic Single Electron Sensors

As described, the present invention provides for single electron structures and the fabrication of such a structures for use in electronic, biologic and chemical devices. The present invention implements an approach that allows for room temperature operation and integration. By incorporating a self-assembling monolayer and aligning the nanoparticles, the present invention is readily available for use in biologic and/or chemical technologies, for example as a biologic or chemical sensor as depicted in FIG. 10.

Figure 10:
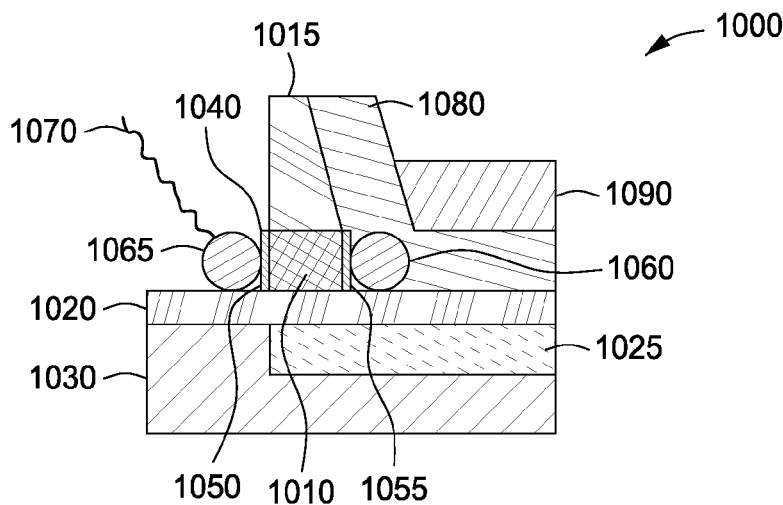
FIG. 10 depicts a schematic of a single electron device of the present invention as a biosensor in accordance with one aspect of the present invention.

As illustrated in FIG. 10, sensor 1000 comprises components found in the single electron structure 100 of FIG. 1, structure 200 of FIG. 2 and structure 900 of FIG. 9. Here, sensing targets are in contact with a portion of the nanoparticles. Sensing targets are not restricted to uniform nanoscale objects, but may include any particles or objects considered to be nanoscale in dimension, such as such as a nucleic acids, amino acids, fatty acids, antibodies, proteins, gas molecules, or natural or synthetic polymers, carbon nanotubes, C60, and other appropriate molecules capable of acting as a sensing target.

Fabrication of structure 1000 follows the method used for fabrication of floating gate structure 900 (single electron memory structure) in which the structure 1000 comprises a substrate 1030 having an upper surface on which first dielectric layer 1020 is formed (FIG. 10). Substrate 1030 is typically monocrystalline silicon, but may comprise any material as previously described. On a portion of first dielectric layer 1020, second dielectric layer 1010 is deposited and defined as is drain 1025. Spacer 1015 is formed and defined on a portion of second dielectric layer 1010. Second dielectric layer 1010 is defined with two exposed sidewalls 1050 and 1055. The thicknesses of second dielectric layer 1010 and first dielectric layer 1020 are typically at least about 10 nm or less; the thickness of first dielectric layer 1020 is generally less than second dielectric layer 1010. A self-assembled monolayer 1040 (equivalent to that previously described) is allowed to form on exposed sidewalls 1050 and 1055 of second dielectric layer 1010. This is followed by immersion of structure 1000 in a solution of nanoparticles to promote attachment of one or more nanoparticles (as illustrated by nanoparticle 1060 and nanoparticle 1065) to monolayer 1040 which has formed on respective sidewalls 1050 and 1055. Nanoparticle 1060 is a charging islands (Coulomb islands) for the single electron structure. Nanoparticle 1065 typically behaves similar to that of a floating gate in the single electron memory structure 900 with a charge that is determined by contact with sensing target 1070.

An additional dielectric material is then added to complete the charging island as shown with fourth dielectric layer 1080, typically through deposition, to a portion of the nanoparticles, in this case, deposition is to sidewall 1055 of second dielectric layer 1010. Fourth dielectric layer 1080 is in contact with nanoparticle 1060, as shown in FIG. 10. After addition of fourth dielectric layer 1080, there is formation of source 1090. To structure 1000, a sensing target 1070 is added. Sensing target may contact nanoparticle 1065 as shown in FIG. 10 or other portions of structure 1000. The contact is typically one of a number of molecular interactions known in the art that include covalent interactions or ionic bonding. The sensor may then be fabricated further, as needed, using techniques known in the art. For example, the sensor may be fabricated into an integrated circuit.

Figure 11A:
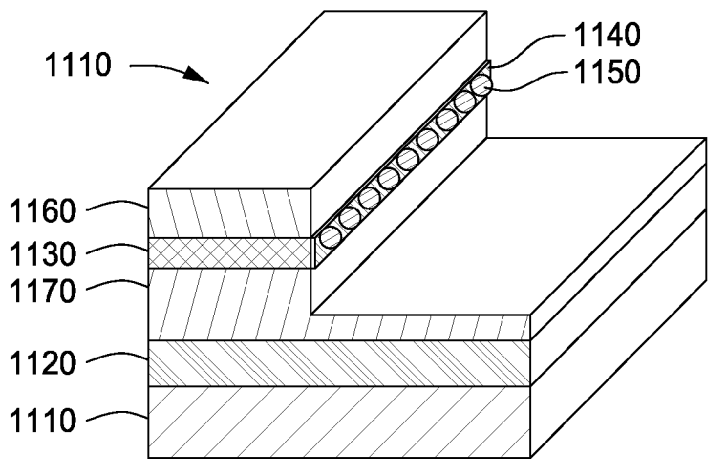
FIGS. 11A and 11B depict schematics of another single electron structure and device of the present invention.
Figure 11B:
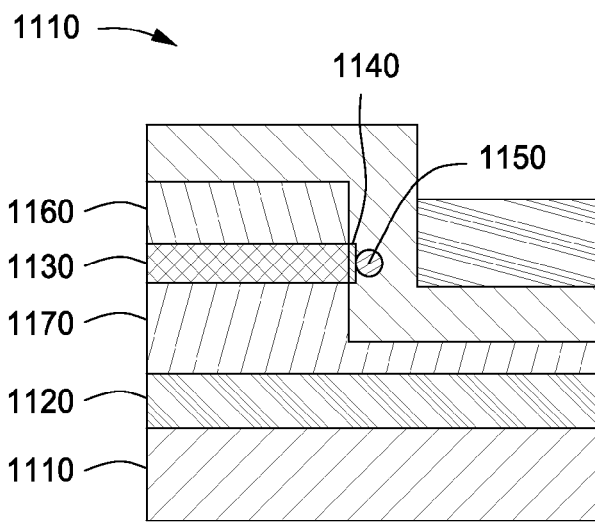

Additional examples of structures and devices of the present invention are depicted in FIGS. 11 and 12. In FIG. 11, a single electron structure and device 1100 is depicted as comprising features similar to those depicted in FIG. 1, FIG. 2, FIG. 9 and FIG. 10 in which a structure or device of the present invention includes a substrate (e.g., layer 1110) having one or more dielectric layers (e.g., layer 1120, layer 1130) on its upper surface, at least one monolayer of self-assembling molecules (e.g., layer 1140) attracted to and in contact with the at least one exposed portion of one of the one or more dielectric layers, one or more nanoparticles (e.g., particles 1150) attracted to and in contact with the at least one monolayer. Additional features include a drain (e.g., layer 1160), a gate (e.g., layer 1180) and a source (e.g., layer 1170). There is a well-defined gap between the source electrode (layer 1170) and drain electrode (layer 1160). This is typically at least about 2 to 20 nm. In addition, nanoparticles 1150 (e.g., Coulomb island) that lie between the source electrode and the drain electrode are precisely positioned. In addition, the distance between gate electrode 1180 and nanoparticles 1150 is precisely controlled. The diameter of nanoparticles is smaller than the gap between source electrode and drain electrode; layer 1130 is greater in diameter than the diameter of the nanoparticles 1150 which provides a tunneling barrier. Accordingly, there exists a gap between the one or more nanoparticles 1150 and the source electrode 1170. Similarly, there exists a gap between the one or more nanoparticles 1150 and the drain electrode 1160. These gaps function as tunneling barriers; the tunneling barriers (e.g., gaps) are filled with material forming a gate dielectric 1190. Examples of materials forming gate dielectric 1190 are silicon dioxide, silicon nitride, hafnium oxide, zirconium oxide and aluminum oxide.

An example of a suitable material for substrate 1110 is silicon; however, any material as previously described may be used as the substrate. Layer 1120 (as depicted in FIG. 11) is typically thicker than that depicted with FIG. 2; such as about 10 nm to 10 micrometer. Layer 1120 is typically comprised of an insulating material, such as silicon dioxide, silicon nitride, sapphire, diamond, as examples. Layer 1130 is typically a dielectric layer onto which charged monolayer 1140 may contact. Layer 1130 is typically at least about 2 to 20 nm.

An example of fabricating a structure 1100 of FIG. 11 is shown in FIG. 12. FIG. 12A depicts structure 1200 comprising substrate 1205 on which layer 1210 is grown or deposited on followed by deposition of layer 1220, which is typically a metal layer comprising any single metal or metal composition. Layer 1225 is a photoresist layer that can be deposited and developed using techniques known to one of ordinary skill in the art. Examples of growth techniques include thermal oxidation or rapid thermal processing. Examples of deposition techniques include chemical vapor deposition (e.g., plasma-enhanced, low-pressure, atomic layer), thermal evaporation, electron beam evaporation, and sputtering. A portion of layer 1225 is defined to form one or more trench 1285, typically by photolithography. On the uppermost surface of layer 1225 and in trench 1285, multiple layers are grown or deposited using techniques known in the art, including first multilayers 1270 and 1275, second multilayers 1230 and 1235 and third multilayers 1260 and 1255 (FIG. 12B). Multilayers 1275, 1235 and 1255 are subsequently removed by lift-off, using techniques known in the art, leaving as defined layers, multilayer 1270, 1230 and 1260 as shown in FIG. 12C. As an alternative, FIG. 12C may be provided by deposition of layers 1210, 1220, 1270, 1230 and 1260, followed by photolithography and dry etching to remove a portion of and to define multilayers 1270, 1230 and 1260. Examples of materials for layers 1220, 1270 and 1260 include gold, ruthenium, chromium, titanium, tantalum, or tungsten. Examples of materials for layer 1230 include silicon dioxide, hafnium oxide, zirconium oxide, aluminum oxide, and low dielectric materials, including those that are porous.

Figure 12A:
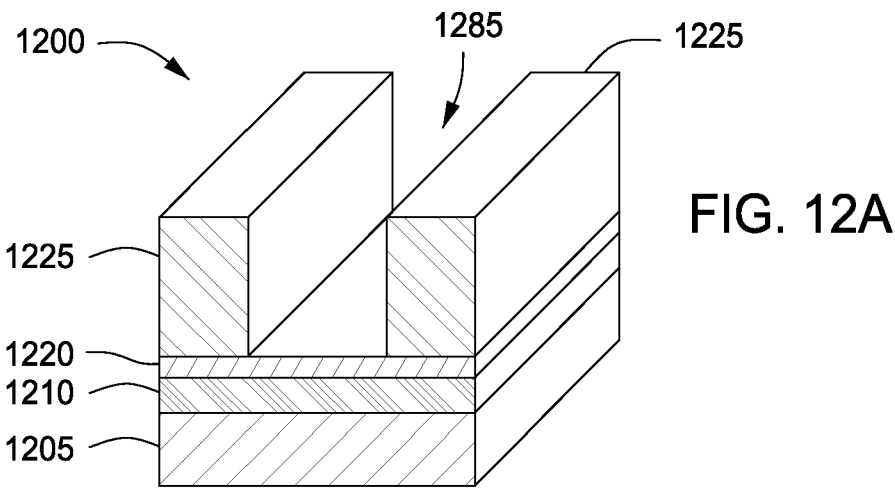
FIGS. 12A-E depict schematics of another fabrication process for a single electron structure and device of the present invention.
Figure 12B:
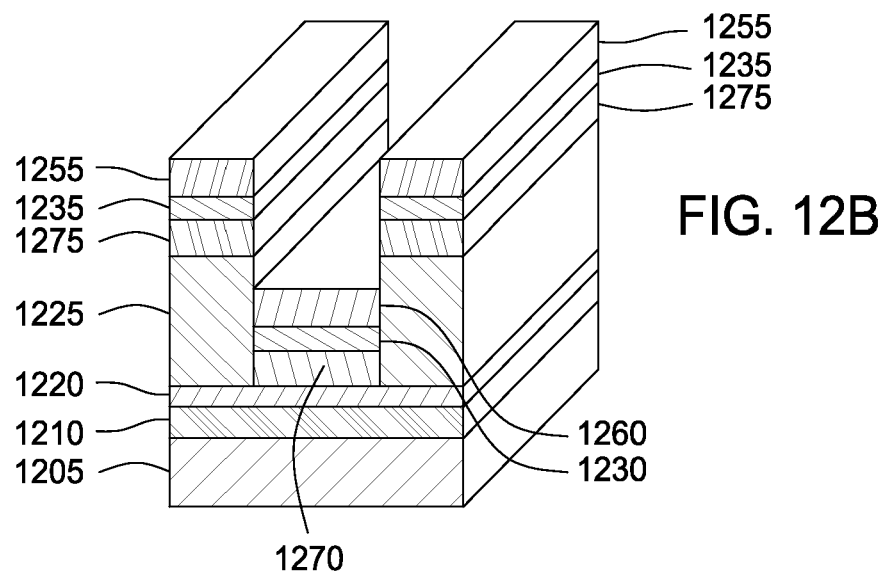
Figure 12C:
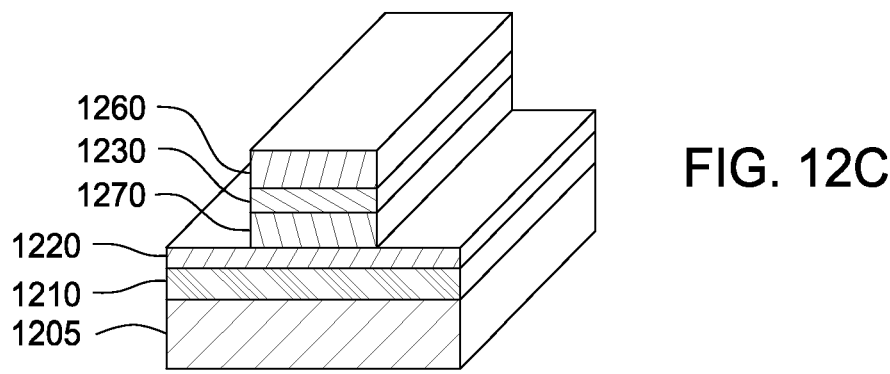
Figure 12D:
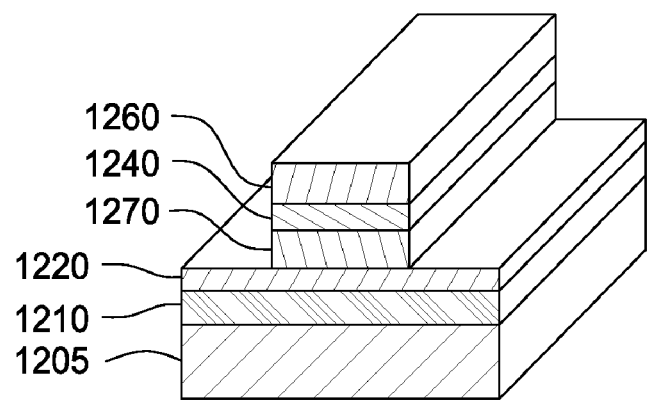
Figure 12E:
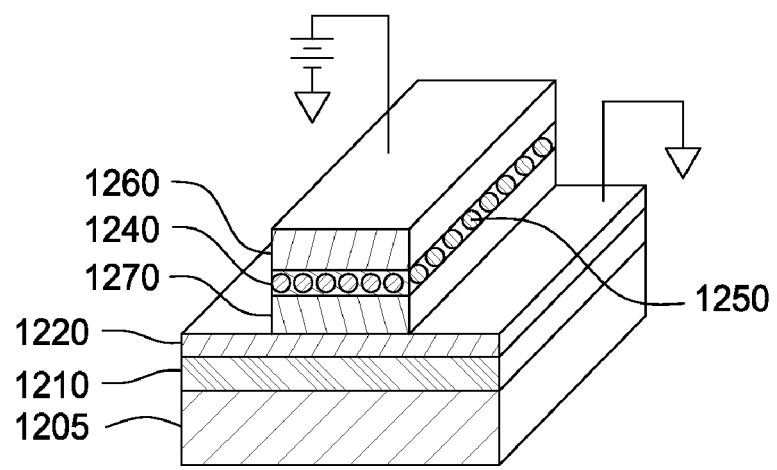

A self-assembled monolayer 1240 is then provided and formed on the sidewall surface of layer 1230 as shown in FIG. 12D. Self-assembled monolayer 1240 is selected based on the choice of second multilayer 1230 deposited on structure 1200; selection requires no undue experimentation. Self-assembled monolayer 1240 must hold an electric charge, be selective for layer 1230, thereby able to selectively form on layer 1230. After assembly of monolayer 1240, substrate 1200 is immersed in a colloidal solution of charged nanoparticles 1250. Because charged nanoparticles 1250 are of an opposite charge to monolayer 1240, nanoparticles 1250 selectively contact monolayer 1240, typically through an electrostatic interaction (FIG. 12E). The thickness of layer 1230 is typically about 2 to 20 nm and is controlled with subnanometer procession. Typically, the thickness of layer 1230 is near or larger than the diameter of the nanoparticles (Coulomb islands). The thickness of layers 1260 and 1270 may vary from tens of nanometers to a few microns. Gaps that exist between nanoparticles 1250 and the source electrode 1270 and between nanoparticles 1250 and the drain electrode 1260 function as tunneling barriers.

As with other examples of the present invention, formation of structure 1100 (FIG. 11) and structure 1200 (FIG. 12) are compatible with current CMOS fabrication processes. In fact, fabrication of the present invention can be readily and easily integrated into current CMOS manufacturing flow.

Further examples of fabrication of the present invention are shown in FIG. 13 and FIG. 14. FIGS. 13A and 13B include scanning electron microscope images of a patterned structure 1300 that includes substrate 1310, a 100 nm layer of gold (layer 1320), a 500 nm layer of silicon oxide (layer 1330), and a 50 nm layer of gold (layer 1340). Gold nanoparticles 1350 contact layer 1330 comprising the monolayer with APTES. FIGS. 14A and 14B include scanning electron microscope images of a patterned structure 1400 that includes substrate 1410, layer 1420—a 150 nm layer of chromium, layer 1430—a 100 nm layer of silicon oxide, layer 1440—a 150 nm layer of chromium. Gold nanoparticles 1450 contact layer 1430 via a monolayer comprising APTES.

While specific alternatives to steps of the invention have been described herein, additional alternatives not specifically disclosed but known in the art are intended to fall within the scope of the invention. Thus, it is understood that other applications of the present invention will be apparent to those skilled in the art upon reading the described embodiment and after consideration of the appended claims and drawing.

What is claimed:

1. A single electron structure comprising:
   a substrate having an upper surface;
   a first dielectric layer formed on the upper surface of the substrate;
   a second dielectric layer defined with an exposed portion and deposited on the first dielectric layer and of a different material than the first dielectric layer;
   a third dielectric layer defined and in contact with the second dielectric and of a different material than the second dielectric layer;

at least one monolayer having self-assembling molecules attracted to and in contact with the exposed portion of the second dielectric layer;
one or more nanoparticles attracted to and in contact with the at least one monolayer; and
a fourth dielectric layer deposited on a portion of the third dielectric layer and the nanoparticles thereby providing a single electron structure exhibiting single electron behavior.

2. The single electron structure of claim 1 wherein the first dielectric layer and the fourth dielectric layer act as tunneling barriers.

3. The single electron structure of claim 1 further comprising a drain, a gate and a source to provide single electron behavior.

4. The single electron structure of claim 3, wherein the drain is implanted on a portion of the substrate either before or after formation of the second dielectric layer.

5. The single electron structure of claim 3, wherein placement of the source and drain is precisely controlled and at least about 10 nm or less.

6. The single electron structure of claim 1, wherein the thickness of the first dielectric layer, second dielectric layer and third dielectric layer are controlled at the subnanometer level.

7. The single electron structure of claim 1, wherein the third dielectric layer acts as a spacer.

8. The single electron structure of claim 1, wherein the one or more nanoparticles consist of materials selected from the group consisting of semiconductor, metal, and combinations thereof.

9. The single electron structure of claim 1, wherein the single electron structure is capable of functioning as a device selected from the group consisting of memory device, logic device, electronic device, biologic sensor, chemical sensor, and combinations thereof.

10. The single electron structure of claim 9, wherein the device is capable of forming an integrated circuit.

11. The single electron structure of claim 1, wherein the second dielectric layer is selected from the group consisting of silicon oxide and aluminum oxide.

12. The single electron structure of claim 1, wherein the self-assembling molecules are selected from the group consisting of glycine and 3-aminopropyltriethoxysilane.

13. The single electron structure of claim 1, wherein the single electron structure is capable of forming an integrated circuit.

14. The single electron structure of claim 1, wherein the single electron structure is fabricated with silicon fabrication technology.

15. A method for fabricating a single electron structure comprising the steps of:
providing a substrate having an upper surface;
forming a first dielectric layer on the upper surface of the substrate;
depositing and defining a second dielectric layer in contact with the first dielectric layer, wherein the second dielectric layer is defined by an exposed portion and is a different material than the first dielectric layer;
forming and defining a third dielectric layer in contact with the second dielectric layer, wherein the third dielectric layer is a different material than the second dielectric layer;
having a monolayer of self-assembling molecules that selectively form on the exposed portion of the second dielectric layer;
providing one or more nanoparticles that contact the self-assembling molecules thereby providing a single electron structure exhibiting single electron behavior.

16. The method of claim 15, wherein the first dielectric layer acts as a tunneling barrier.

17. The method of claim 15 further comprising adding a fourth dielectric layer on the one or more nanoparticles as a tunneling barrier.

18. The method of claim 17 further comprising the step of forming a drain, a gate and a source to provide single electron behavior.

19. The method of claim 18, wherein the drain is implanted on a portion of the substrate either before or after formation of the second dielectric layer.

20. The method of claim 18, wherein placement of the source and drain is precisely controlled and at least about 10 nm apart or less.

21. The method of claim 15, wherein the thickness of first dielectric layer, second dielectric layer and third dielectric layer are controlled at the subnanometer level.

22. The method of claim 15, wherein the third dielectric layer acts as a spacer.

23. The method of claim 15, wherein the one or more nanoparticles consist of materials selected from the group consisting of semiconductor, metal, and combinations thereof.

24. The method of claim 15, wherein the single electron structure is capable of functioning as a device selected from the group consisting of memory device, logic device, electronic device, biologic sensor, chemical sensor, and combinations thereof.

25. The method of claim 24, wherein the device is capable of forming an integrated circuit.

26. The method of claim 15, wherein the second dielectric layer is selected from the group consisting of silicon oxide and aluminum oxide.

27. The method of claim 15, wherein the self-assembling molecules are selected from the group consisting of glycine and 3-aminopropyltriethoxysilane.

28. The method of claim 15, wherein the single electron structure is fabricated with silicon fabrication technology.

29. The method of claim 28, wherein the single electron memory is capable of forming an integrated circuit.

30. A single electron structure comprising:
a substrate having an upper surface;
a first dielectric layer formed on the upper surface of the substrate;
a second dielectric layer defined with exposed portions and deposited on the first dielectric layer and of a different material than the first dielectric layer;
a third dielectric layer defined and in contact with the second dielectric and of a different material than the second dielectric layer;
at least one self-assembled monolayer attracted to and in contact with exposed portions of the second dielectric layer;
one or more nanoparticles attracted to and in contact with the at least one self-assembled monolayer thereby providing a single electron memory device exhibiting single electron memory behavior.

31. The single electron structure of claim 30, wherein the first dielectric layer acts as a tunneling barrier.

32. The single electron structure of claim 30 further comprising a fourth dielectric layer formed on the one or more nanoparticles as a tunneling barrier.

33. The single electron structure of claim 32 further comprising a drain, a gate and a source to provide single electron behavior.

34. The single electron structure of claim 33, wherein the drain is implanted on a portion of the substrate either before or after formation of the second dielectric layer.

35. The single electron structure of claim 30, wherein the thickness of the first dielectric layer, second dielectric layer and third dielectric layer are controlled at the subnanometer level.

36. The single electron structure of claim 30, wherein the third dielectric layer acts as a spacer.

37. The single electron structure of claim 30, wherein the one or more nanoparticles consist of materials selected from the group consisting of semiconductor, metal, and combinations thereof.

38. The single electron structure of claim 30, wherein the single electron structure is capable of forming an integrated circuit.

39. The single electron structure of claim 30, wherein the single electron structure is a single electron memory with a floating gate.

40. The single electron structure of claim 39, wherein the single electron memory device is capable of forming an integrated circuit.

41. A method of selective positioning of nanoparticles on a single electron structure comprising the steps of:
forming a self-assembled monolayer on a portion of a single electron structure, wherein the self-assembled monolayer is capable of selectively recognizing only a portion of the single electron structure; and
contacting the self-assembled monolayer with at least one nanoparticle to provide a single electron structure exhibiting single electron behavior.

42. The method of claim 41, wherein the at least one nanoparticle consists of a material selected from the group consisting of semiconductor, metal, and combinations thereof.

43. The method of claim 41 further comprising forming a fourth dielectric layer on the one or more nanoparticles as a tunneling barrier.

44. The method of claim 41, wherein the single electron structure is capable of functioning as a device selected from the group consisting of memory device, logic device, electronic device, biologic sensor, chemical sensor, and combinations thereof.

45. The method of claim 44, wherein the device is capable of forming an integrated circuit.

46. The method of claim 41 further comprising removing the self-assembled monolayer after contacting the at least one nanoparticle.

47. A single electron structure comprising:
a substrate having an upper surface;
one or more dielectric layers formed on the upper surface of the substrate and having at least one exposed portion;
at least one monolayer of self-assembling molecules attracted to and in contact with the at least one exposed portion of only one of the one or more dielectric layers;
one or more nanoparticles attracted to and in contact with the at least one monolayer;
at least one tunneling barrier in contact with the one or more nanoparticles to provide single electron behavior.

48. The single electron structure of claim 46 further comprising a drain, a gate and a source to provide single electron behavior, wherein there is a defined gap between source and drain and the one or more nanoparticles is positioned between the source and drain.

49. The single electron structure of claim 48, wherein the defined gap between source and drain is at least about 10 nm or less.

50. The single electron structure of claim 47, wherein the single electron structure is capable of forming an integrated circuit.

51. A single electron structure comprising:
a substrate having an upper surface;
one or more dielectric layers formed on the upper surface of the substrate and having at least one exposed portion;
at least one monolayer of self-assembling molecules attracted to and in contact with the at least one exposed portion of only one of the one or more dielectric layers; and
one or more nanoparticles attracted to and in contact with the at least one monolayer;
a drain, a gate and a source to provide single electron behavior.

52. The single electron structure of claim 51, wherein there is a defined gap between the source and the one or more nanoparticles and between the drain and the one or more nanoparticles that provide a tunneling barrier.

53. The single electron structure of claim 51, wherein a distance between the gate and the one or more nanoparticles is precisely controlled.

* * * * *

UNITED STATES PATENT AND TRADEMARK OFFICE
CERTIFICATE OF CORRECTION

PATENT NO. : 7,465,953 B1
APPLICATION NO. : 11/412273
DATED : December 16, 2008
INVENTOR(S) : Koh et al.

It is certified that error appears in the above-identified patent and that said Letters Patent is hereby corrected as shown below:

Title page Item (54)
Replace "POSITIONING OF NANOPARTICLES AND FABRICATION OF SINGLE ELECTION DEVICES" with --POSITIONING OF NANOPARTICLES AND FABRICATION OF SINGLE ELECTRON DEVICES--

Title page Item (75)
Replace "Ramkumar Subramaniam, Dallas, TX (US)" with --Ramkumar Subramaniam, Arlington, TX (US)--

Title page Item (74)
Replace "Gardere Wynne Sewell LLP" with --Chalker Flores, LLP; Daniel J. Chalker; Edwin S. Flores--

Col. 1, line 2
Replace "Single Election" with --Single Electron--

Col. 1, line 39
Replace "of an SET must" with --of a SET must--

Col. 4, line 22
Replace "FIGS. 12A-E depict" with --FIGS. 12A-12E depict--

Col. 5, line 4
Replace "An SET is" with --A SET is--

Col. 7, line 54
Replace "atomic layer deposition [ALD])" with --atomic layer deposition [ALD]--

Col. 8, line 40
Replace "285 selectively contacted monolayer" with --285 selectively contacts monolayer--

Col. 10, line 10
Replace "An advantages of aluminium oxide it that it" with --An advantage of aluminium oxide is that it--

UNITED STATES PATENT AND TRADEMARK OFFICE
CERTIFICATE OF CORRECTION

PATENT NO. : 7,465,953 B1
APPLICATION NO. : 11/412273
DATED : December 16, 2008
INVENTOR(S) : Koh et al.

It is certified that error appears in the above-identified patent and that said Letters Patent is hereby corrected as shown below:

Col. 10, line 29
Replace "was exposed A monolayer 540" with --was exposed. A monolayer 540--

Col. 11, line 11
Replace "AFM images was taken of" with --AFM images taken of--

Col. 11, line 33
Replace "detected using an SET. Because" with --"detected using a SET. Because--

Signed and Sealed this

Twenty-sixth Day of May, 2009

JOHN DOLL
*Acting Director of the United States Patent and Trademark Office*